United States Patent
Lim

(10) Patent No.: US 9,999,411 B2
(45) Date of Patent: Jun. 19, 2018

(54) VASCULAR CLOSURE DEVICE WITH A PLUG HAVING A VARIABLE EXPANSION RATE AND METHOD FOR USING THE SAME

(75) Inventor: JyueBoon Lim, New Brighton, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 274 days.

(21) Appl. No.: 14/116,693

(22) PCT Filed: May 16, 2012

(86) PCT No.: PCT/US2012/038033
§ 371 (c)(1),
(2), (4) Date: Dec. 11, 2013

(87) PCT Pub. No.: WO2012/158740
PCT Pub. Date: Nov. 22, 2012

(65) Prior Publication Data
US 2014/0094846 A1 Apr. 3, 2014

Related U.S. Application Data

(60) Provisional application No. 61/487,997, filed on May 19, 2011.

(51) Int. Cl.
*A61B 17/00* (2006.01)

(52) U.S. Cl.
CPC ........ *A61B 17/0057* (2013.01); *A61B 2017/00588* (2013.01); *A61B 2017/00592* (2013.01);
(Continued)

(58) Field of Classification Search
CPC ...... A61B 17/0057; A61B 2017/00588; A61B 2017/00592; A61B 2017/00623;
(Continued)

(56) References Cited

U.S. PATENT DOCUMENTS 5,053,046 A * 10/1991 Janese ............... A61B 17/3401
604/506
6,183,496 B1 2/2001 Urbanski
(Continued)

FOREIGN PATENT DOCUMENTS

WO 0110306 A1 2/2001

OTHER PUBLICATIONS

PCT International Search Report for PCT International Patent Application No. PCT/US2012/038033, dated Sep. 12, 2012.

*Primary Examiner* — Julie A Szpira
(74) *Attorney, Agent, or Firm* — Dorsey & Whitney LLP

(57) ABSTRACT

A vascular closure device, having an insertion sheath and a vascular closure implant positioned at least partially in the insertion sheath. The vascular closure implant may have an anchor element, the anchor element including an expandable material, a first puncture contact portion, a bend portion connected to the first puncture contact portion, the bend portion including a bend, and a second puncture contact portion connected to the bend portion. The vascular closure implant may also include a plug element coupled to the bend portion of the anchor element. The anchor element may be formed of an expandable material having the same or a different expansion rate than a material forming the plug element. The vascular closure device may additionally include a locator tube having a vessel locator positioned at least partially in the locator tube. The vessel locator may also have an elongated member that includes a superelastic material.

18 Claims, 11 Drawing Sheets

(52) U.S. Cl.
CPC ............... *A61B 2017/00623* (2013.01); *A61B 2017/00654* (2013.01); *A61B 2017/00672* (2013.01); *A61B 2017/00898* (2013.01)

(58) Field of Classification Search
CPC ........... A61B 2017/00654; A61B 2017/00672; A61B 2017/00898
See application file for complete search history.

(56) References Cited

U.S. PATENT DOCUMENTS

| | | | | |
|---|---|---|---|---|
| 6,692,506 | B1* | 2/2004 | Ory | A61B 17/064 606/144 |
| 2002/0072767 | A1* | 6/2002 | Zhu | A61B 17/0057 606/213 |
| 2005/0155608 | A1* | 7/2005 | Pavcnik | A61B 17/12022 128/831 |
| 2005/0267528 | A1* | 12/2005 | Ginn | A61B 17/0057 606/214 |
| 2007/0191884 | A1* | 8/2007 | Eskridge | A61B 17/12022 606/213 |
| 2008/0065151 | A1* | 3/2008 | Ginn | A61B 17/0057 606/213 |
| 2010/0198254 | A1* | 8/2010 | Schaeffer | A61B 17/0057 606/213 |
| 2011/0270282 | A1* | 11/2011 | Lemke | A61B 17/0057 606/148 |
| 2012/0010653 | A1* | 1/2012 | Seifert | A61B 17/0057 606/213 |

* cited by examiner

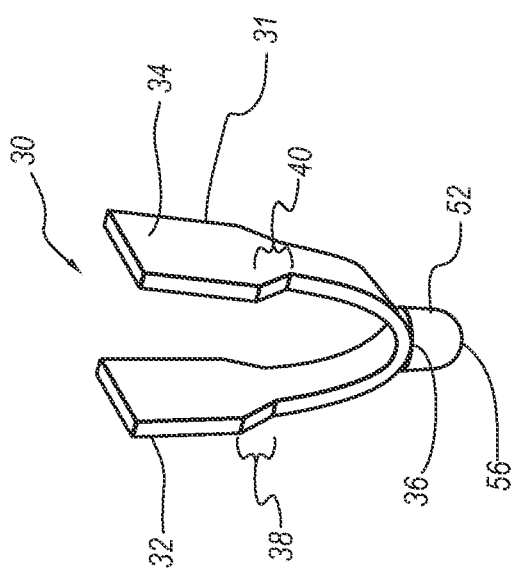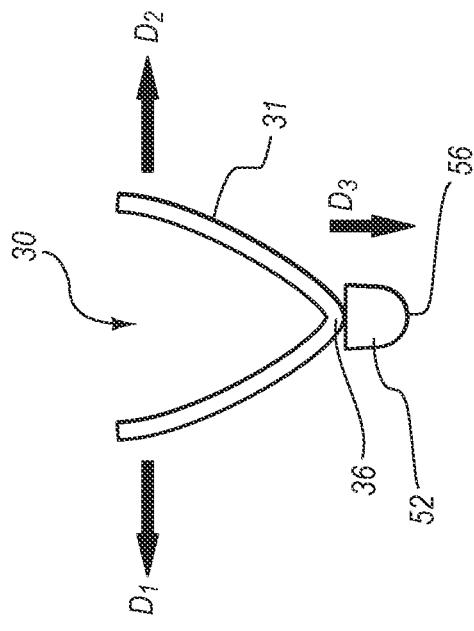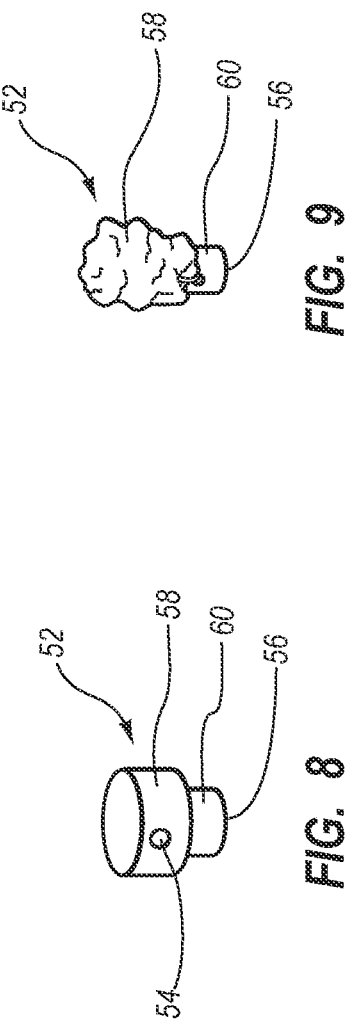
FIG. 5
FIG. 6
FIG. 7
FIG. 8
FIG. 9

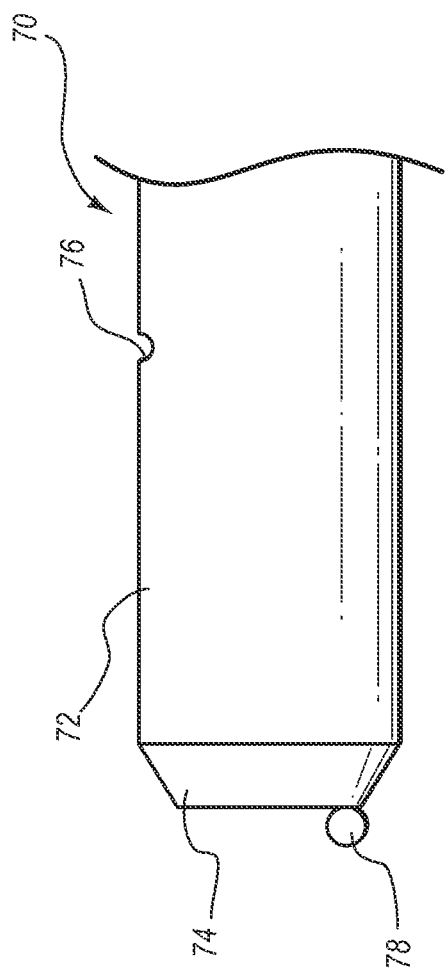
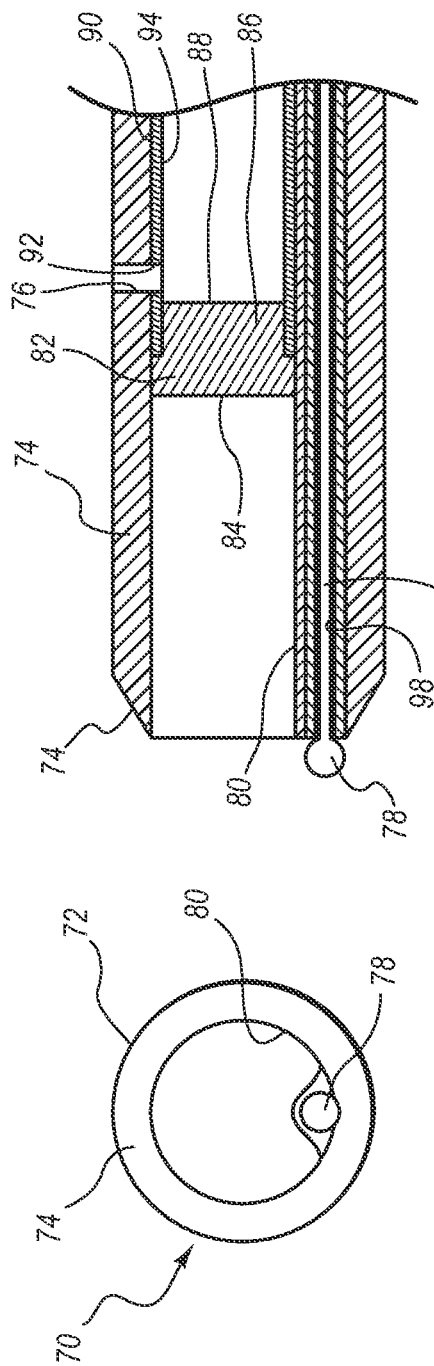

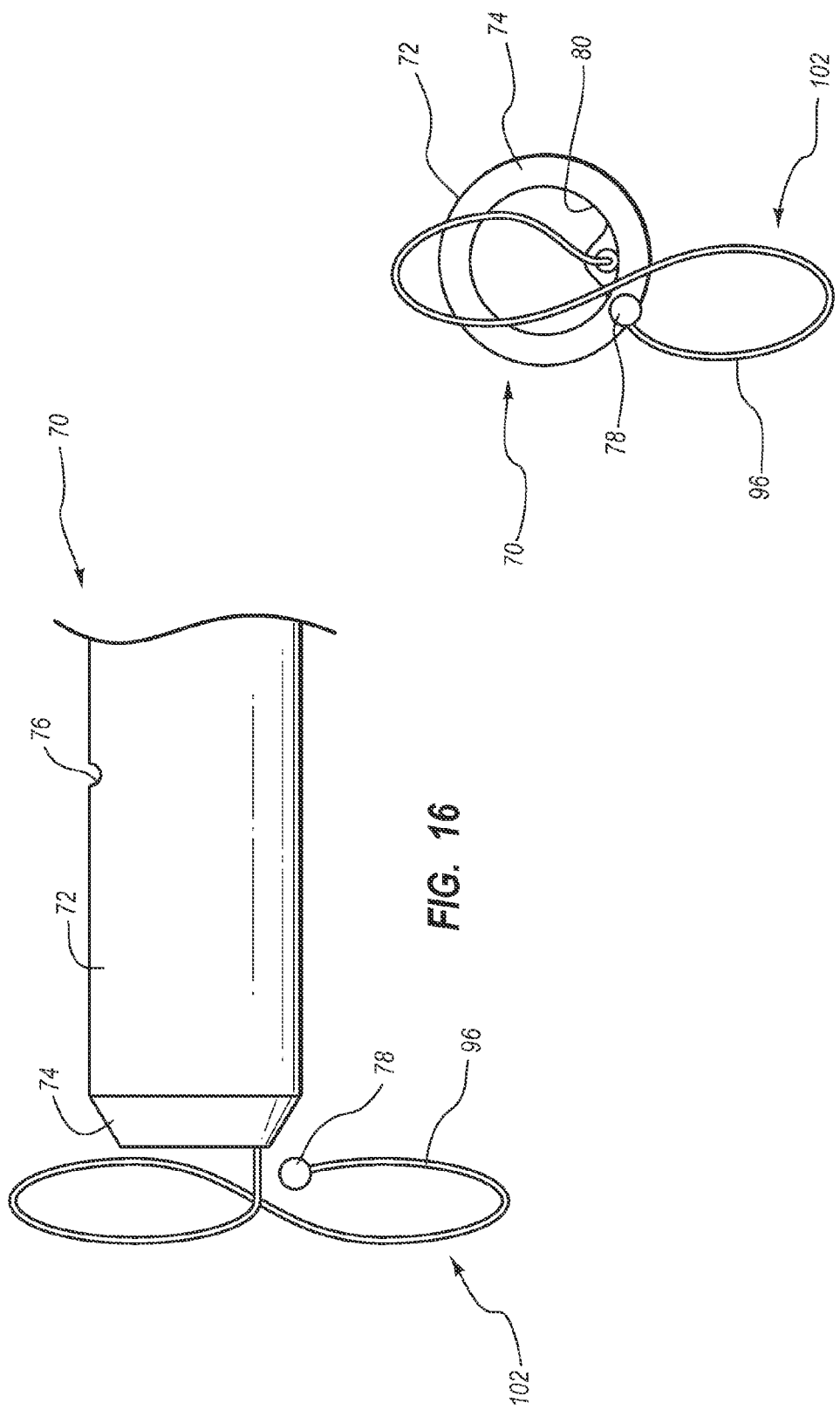

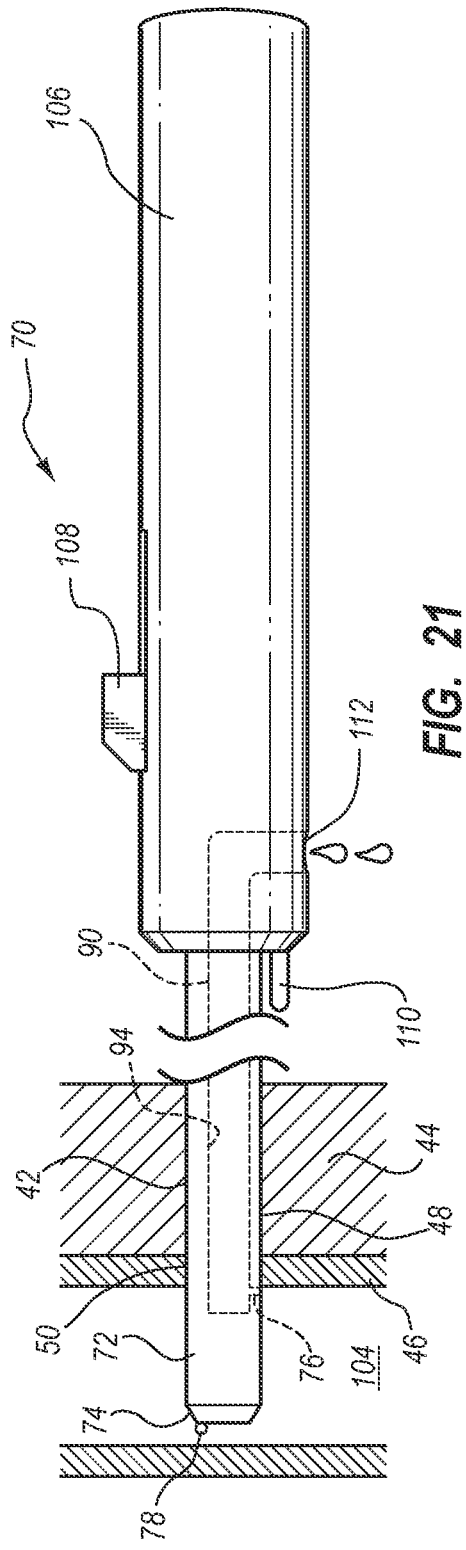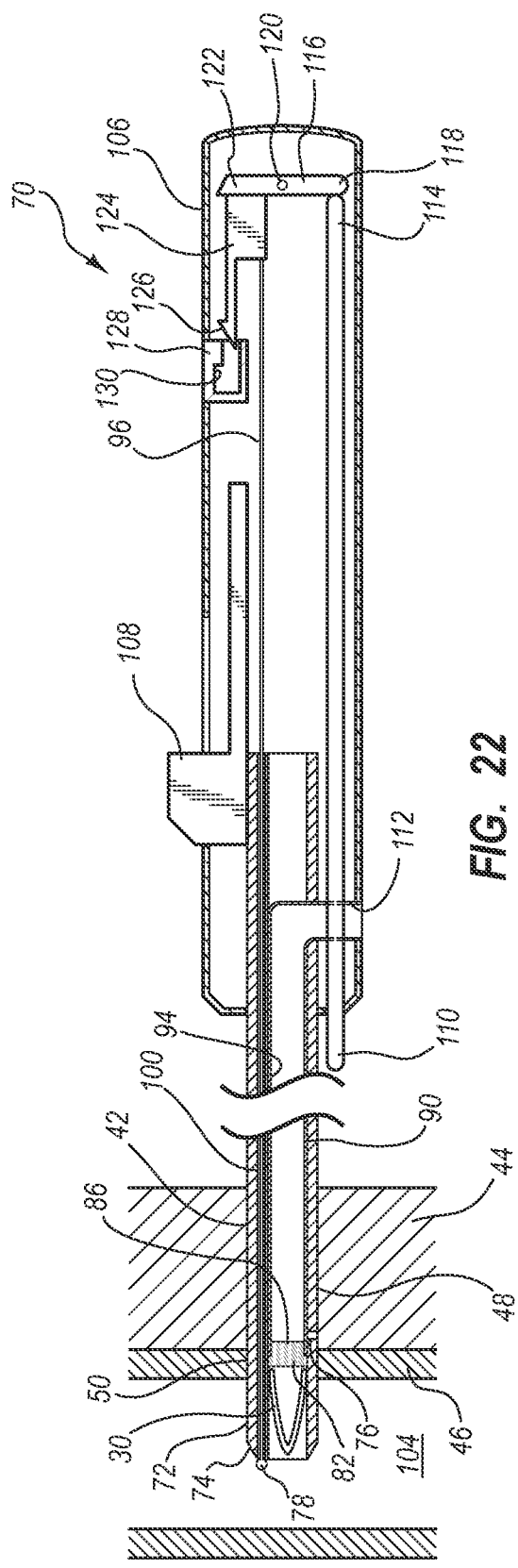

VASCULAR CLOSURE DEVICE WITH A PLUG HAVING A VARIABLE EXPANSION RATE AND METHOD FOR USING THE SAME

RELATED APPLICATION

This claims the benefit of U.S. Provisional Application No. 61/487,997, filed 19 May 2011, which is hereby incorporated by reference herein in its entirety.

BACKGROUND

Catheter based diagnostic and interventional procedures such as angiograms, balloon angioplasty, stenting, atherectomy, thrombectomy, device placement, etc., are commonly employed to treat patients with vascular obstructions or other abnormalities accessible through the vasculature of the human body. Such interventions are less traumatic to the body than previous surgical interventions and therefore are growing in use.

Following various diagnostic and interventional procedures, and after equipment used to perform the procedure has been removed from the patient, manual pressure is often applied directly to the skin above the access puncture for about thirty minutes to inhibit blood loss until the body's natural clotting process seals the puncture. However, this technique may result in discomfort to the patient and may require a significant amount of nursing staff time.

Additionally, various vascular closure devices have been used that deposit a plug in the proximity of a vessel. Unfortunately, these devices suffer from a number of drawbacks. For example, the pressure exerted on the plug can cause the plug to move away from the vessel puncture site, resulting in a hemotoma or other complication at the puncture site. Also, the plug may not seal the puncture tract/hole in the blood vessel sufficiently to prevent leakage. Additionally, these devices may present difficulties in properly positioning the plug relative to the vessel puncture.

SUMMARY

According to at least one embodiment, a vascular closure implant may comprise an anchor element, the anchor element comprising an expandable material, a first puncture contact portion, a bend portion connected to the first puncture contact portion, the bend portion including a bend, and a second puncture contact portion connected to the bend portion. The vascular closure implant may also comprise a plug element coupled to the bend portion of the anchor element, the plug element comprising an expandable material.

According to additional embodiments, a vascular closure implant may comprise an anchor element, the anchor element comprising an absorbent material, a first puncture contact portion, a bend portion connected to the first puncture contact portion, the bend portion including a bend, and a second puncture contact portion connected to the bend portion.

According to various embodiments, a vascular closure device may comprise an insertion sheath and a vascular closure implant having an anchor element positioned at least partially in the insertion sheath. The anchor element may comprise an absorbent material, a first puncture contact portion, a bend portion connected to the first puncture contact portion, the bend portion including a bend, and a second puncture contact portion connected to the bend portion.

According to at least one embodiment, a vascular closure device may comprise a locator tube and a vessel locator positioned at least partially in the locator tube. The vessel locator may comprise an elongated member comprising a superelastic material and a first locator portion having an original shape. The vascular closure device may also comprise a vascular closure implant.

According to certain embodiments, a method of deploying a vascular closure implant in a puncture tract may include providing a vascular closure device comprising a locator tube and a vessel locator positioned at least partially in the locator tube. The vessel locator may comprise an elongated member comprising a superelastic material and a first locator portion having an original shape. The vessel locator may also comprise a vascular closure implant. The method of deploying a vascular closure implant in a puncture tract may also comprise inserting the vessel locator into a vessel such that the first locator portion is located outside the locator tube and positioning the vessel locator such that the first locator portion contacts the inside wall of the vessel.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIG. 5 is a perspective view of a vascular closure implant according to an additional embodiment;

FIG. 6 is a side view of a vascular closure implant according to an additional embodiment;

FIG. 7 is a perspective view of a plug element according to at least one embodiment;

FIG. 8 is a perspective view of a plug element according to an additional embodiment;

FIG. 9 is a perspective view of a plug element according to an additional embodiment;

FIG. 12 is a side view of a distal end of a vascular closure device according to at least one embodiment;

FIG. 13 is a front view of a distal end of a vascular closure device according to an additional embodiment;

FIG. 14 is a cross-sectional view of a distal end portion of a vascular closure device according to an additional embodiment;

FIG. 16 is a side view of a distal end portion of a vascular closure device according to an additional embodiment;

FIG. 17 is a front view of a distal end portion of a vascular closure device according to an additional embodiment;

FIG. 21 is a side view of a vascular closure device disposed in a puncture tract according to an additional embodiment;

FIG. 22 is a cross-sectional side view of a vascular closure device disposed in a puncture tract according to an additional embodiment;

Figure 1:
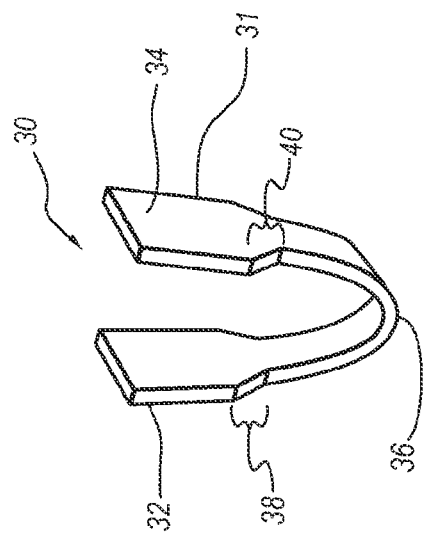
FIG. 1 is a perspective view of a vascular closure implant according to at least one embodiment.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

A number of embodiments of vascular closure devices are shown and described herein. In various embodiments, the vascular closure devices may be used to close a hole or puncture in a blood vessel such as an arteriotomy. In additional embodiments, the vascular closure devices may be hemostatic devices that are used to stop bleeding from vascular puncture sites following percutaneous diagnostic or therapeutic procedures.

In various embodiments, the vascular closure devices may be configured to deploy one or more vascular closure implants outside of a blood vessel adjacent to a vessel puncture site. Additionally, the vascular closure devices may be configured to deploy one or more vascular closure implants in a puncture tract adjacent to a vessel puncture site. The vascular closure implant may block a hole at a puncture site in the blood vessel and/or a puncture tract to prevent and/or stop from the vessel bleeding.

In at least one embodiment, the vascular closure implant may be configured to prevent the vascular closure implant from moving away from the puncture site in the blood vessel due to pulses in the blood pressure. For example, the vascular closure implant may be shaped to allow the vascular closure implant to move toward the blood vessel and prevent and/or impede the vascular closure implant from moving away from the blood vessel. The vascular closure implant may include a plurality of projections, such as barbs, that extend outward from the vascular closure implant to contact surrounding tissue to prevent the vascular closure implant from moving away from the blood vessel. In at least one embodiment, the vascular closure implant may comprise a bioabsorbable polymer, such as, for example, polyglycolic acid ("PGA") materials, polyethylene glycol ("PEG") materials, and/or polylactic acid ("PLA") materials. The vascular closure implant may also be configured to hold its shape in the presence of various bodily fluids. A combination of these materials can be used to create a bioabsorbable polymer.

In additional embodiments, the vascular closure implant may be deployed with and/or coupled to a closure material such as protein-based sealing materials (e.g., collagen, fibrinogen, thrombin, and the like), which may also be bioabsorbable. Protein-based sealing materials, such as, for example, collagen may swell and/or expand in the presence of various fluids, such as fluids present in blood. Additionally, protein-based sealing materials, such as, for example, collagen, may swell in the presence of a fluid other than blood that is introduced to the site of a vascular closure implant.

FIG. 1 is an exemplary vascular closure implant 30 according to at least one embodiment. As illustrated in this figure, vascular closure implant 30 may comprise an anchor element 31 having a first puncture contact portion 32, a bend portion 36, and a second puncture contact portion 34. In at least one embodiment, first puncture contact portion 32 may be connected to bend portion 36, which may additionally be connected to second puncture contact portion 34.

In various embodiments, first puncture contact portion 32 and second puncture contact portion 34 may represent portions of vascular closure implant 30 configured to contact a puncture tract wall in a tissue puncture tract. For example, first puncture contact portion 32 and second puncture contact portion 34 may comprise end portions of vascular closure implant 30 and/or surfaces of vascular closure implant 30 proximate to the end portions.

Bend portion 36 may comprise a portion of vascular closure implant 30 that is formed in a bent, curved, and/or angled shape. Bend portion 36 may be formed by applying force to vascular closure implant 30, causing vascular closure implant 30 to bend and/or fold to form bend portion 36. In various embodiments, bend portion 36 may be formed in vascular closure implant 30 by folding a generally straight piece of material under force. For example, vascular closure implant 30 may be formed by bending a relatively thin, flat, and elongated object, such as a generally rectangular object. Optionally, vascular closure implant 30 may be molded and/or otherwise formed to include a curved portion, after which additional force may be applied to form bend portion 36. In various embodiments, vascular closure implant 30 may be formed to a generally "U" and/or a generally "V" shaped configuration, where vascular closure implant 30 is folded and/or bent at one portion. As will be described in greater detail below, bend portion 36 may be formed, and subsequently vascular closure implant 30 may be placed within a retaining structure to maintain bend portion 36 in a bent configuration.

Vascular closure implant 30 may comprise any suitable material or combination of materials, without limitation. In at least one embodiment, vascular closure implant may comprise an absorbent material that may swell and/or expand when introduced into a puncture tract. Such materials may include, without limitation, collagen materials and/or other protein-based materials. Collagen materials may swell and/or expand in the presence of various fluids such as, for example, fluids present in blood. As will be described in greater detail below, a material such as collagen may exert various forces on a puncture tract and/or a vessel puncture site based on the geometry of vascular closure implant 30 (e.g., a folded configuration that includes bend portion 36). Additionally, a material such as collagen may exert various forces on a puncture tract and/or a vessel puncture site due to the swelling and/or expanding of the vascular closure implant 30.

Figure 2:
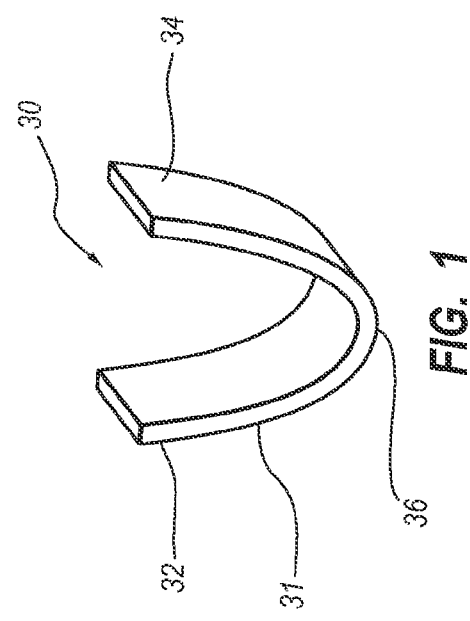
FIG. 2 is a perspective view of a vascular closure implant according to an additional embodiment.

FIG. 2 is an exemplary vascular closure implant 30 according to an additional embodiment. As illustrated in this figure, vascular closure implant 30 may comprise an anchor element 31 having a bend portion 36, a first puncture contact portion 32, and a second puncture contact portion 34. In addition, vascular closure implant 30 may comprise a first taper portion 38 and a second taper portion 40.

First taper portion 38 may comprise a portion of vascular closure implant 30 located between first puncture contact portion 32 and bend portion 36. Similarly, second taper portion 40 may comprise a portion of vascular closure implant 30 located between second puncture contact portion 34 and bend portion 35. First taper portion 38 and second taper portion 40 may represent portions of vascular closure implant 30 where a width of vascular closure implant 30 tapers from a wider to a narrower portion. For example, first puncture contact portion 32 and second puncture contact portion 34 may each be wider than bend portion 36. It may be desirable, for instance, to form first puncture contact portion 32 and second puncture contact portion 34 to a width that maximizes the contact area between vascular closure implant 30 and a puncture tract wall. It may further be desirable, for instance, to form bend portion 36 to a narrower width than first puncture contact portion 32 and/or second puncture contact portion 34 in order to optimize an amount of force exerted by bend portion 36.

Figure 3:
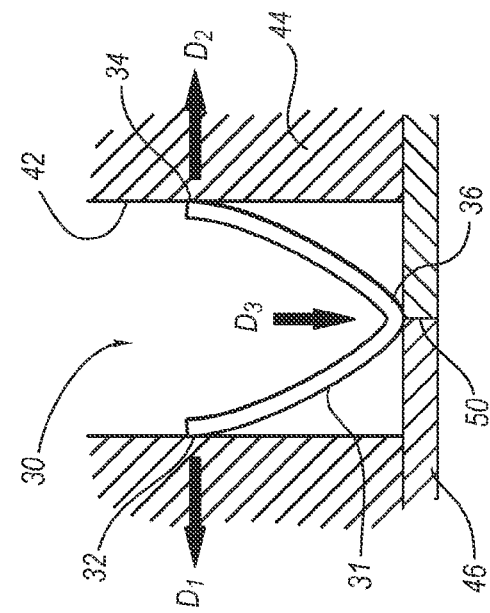
FIG. 3 is a side view of a vascular closure implant disposed in a puncture tract according to an additional embodiment.

FIG. 3 is an exemplary vascular closure implant 30 that is disposed in a puncture tract 48 according to an additional embodiment. As illustrated in this figure, vascular closure implant 30 may be positioned and deployed in puncture tract 48 within tissue 44. Vascular closure implant 30 may be positioned adjacent puncture tract wall 42. Additionally, first puncture contact portion 32 and second puncture contact portion 34 may abut portions of puncture tract wall 42 and may exert force on puncture tract wall 42, effectively anchoring vascular closure implant 30 in puncture tract 48. For example, first puncture contact portion 32 and second puncture contact portion 34 may exert force on puncture tract wall 42 generally in directions $D_1$ and $D_2$.

Force may be exerted on first puncture contact portion 32 and second puncture contact portion 34 by bend portion 36. In various embodiments, bend portion 36 may exert force on first puncture contact portion 32 and second puncture contact portion 34 through a spring like effect. In other words, bend portion 36, and/or other portions of vascular closure implant 30, may essentially store mechanical energy when vascular closure implant 30 is bent and/or otherwise deformed prior to being positioned and/or deployed in puncture tract 48. When the vascular closure implant 30 is deployed in puncture tract 48, mechanical energy stored in bend portion 36 of vascular closure implant 30 may exert force on first puncture contact portion 32 and second puncture contact portion 34, causing first puncture contact portion 32 and second puncture contact portion 34 to move toward puncture tract wall 42 and exert force against puncture tract wall 42 generally in directions $D_1$ and $D_2$.

By exerting force on puncture tract wall 42, such as in general directions $D_1$ and $D_2$, first puncture contact portion 32 and second puncture contact portion 34 may be tightly positioned against puncture tract wall 42, anchoring vascular closure implant 30 in puncture tract 48. Additionally, first puncture contact portion 32 and second puncture contact portion 34 may exert force on puncture tract wall 42 sufficient to compress at least a portion of tissue 44 proximate to first puncture contact portion 32 and second puncture contact portion 34, further anchoring vascular closure implant 30 in puncture tract 48.

In an additional embodiment, as described above, vascular closure implant 30 may comprise a material that may swell and/or expand when introduced into a puncture tract, such as, for example, a collagen material. A vascular closure implant 30 formed from a material that may swell and/or expand when introduced into puncture tract 48 may exert various forces on puncture tract 48 due to swelling and/or expanding of the vascular closure implant 30. The swelling and/or expanding action of vascular closure implant 30 may further increase the forces exerted by vascular closure implant 30 on puncture tract wall 42 of puncture tract 48, particularly in combination with the forces exerted by vascular closure implant 30 due to the mechanical energy stored in bend portion 36. Additionally, the swelling and/or expanding action of vascular closure implant 30 may also increase the surface area of the vascular closure implant 30 contacting puncture tract wall 42.

Figure 4:
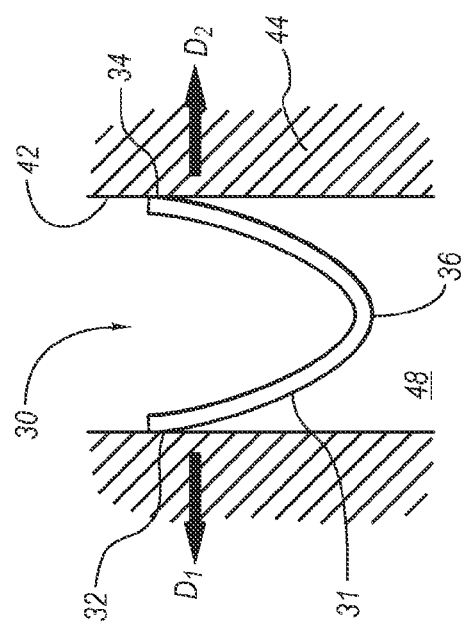
FIG. 4 is a side view of a vascular closure implant disposed in a puncture tract according to an additional embodiment.

FIG. 4 is an exemplary vascular closure implant 30 that is disposed in a puncture tract according to an additional embodiment. As illustrated in this figure, vascular closure implant 30 may be positioned and deployed in a puncture tract 48 within tissue 44. Vascular closure implant 30 may be positioned adjacent puncture tract wall 42. First puncture contact portion 32 and second puncture contact portion 34 may abut portions of puncture tract wall 42 and may exert force on puncture tract wall 42. For example, first puncture contact portion 32 and second puncture contact portion 34 may exert force on puncture tract wall 42 generally in directions $D_1$ and $D_2$.

Additionally, vascular closure implant 30 may be positioned adjacent a vessel wall 46. As shown in FIG. 4, vascular closure implant 30 may be positioned abutting vessel wall 46 at and/or proximate to the site of a vessel puncture 50 in vessel wall 46. Bend portion 36, and/or a portion of vascular closure implant 30 near bend portion 36, may abut vessel wall 46. Additionally, vascular closure implant 30 may exert a force against vessel wall 46 generally in direction $D_3$ to at least partially close vessel puncture 50. By exerting a force against vessel wall 46 proximate to vessel puncture 50 generally in direction $D_3$, vascular closure implant 30 may also counteract forces exerted by blood flowing through a vessel comprising vessel wall 46. In additional embodiments, a portion of vascular closure implant 30 may at least partially fill a portion of vessel puncture 50, effectively plugging at least a portion of vessel puncture 50.

By exerting force on vessel wall 46, such as in general direction $D_3$, vascular closure implant 30 may at least partially close and/or at least partially seal vessel puncture 50, thereby preventing blood from migrating through vessel puncture 50 into puncture tract 48. In various embodiments, as described above, vascular closure implant 30 may comprise a material that may swell and/or expand when introduced into a puncture tract, such as, for example, a collagen material. A vascular closure implant 30 formed from a material that may swell and/or expand when introduced into puncture tract 48 may exert various forces on vessel wall 46 due to swelling and/or expanding of the vascular closure implant 30. The swelling and/or expanding action of vascular closure implant 30 may further increase the force exerted by vascular closure implant 30 on vessel wall 46. Additionally, the swelling and/or expanding action of vascular closure implant 30 may also increase the surface area of the vascular closure implant 30 contacting vessel wall 46.

In various embodiments, the orientation of vascular closure implant 30 may facilitate introduction of vascular closure implant 30 into puncture tract 48, while preventing displacement of vascular closure implant 30 from puncture tract 48. For example, vascular closure implant 30 may comprise less resistance from puncture tract wall 42 be being introduced into puncture tract 48 with bend portion 36 facing the direction of introduction into puncture tract 48 (i.e., generally in direction $D_3$). Additionally, first puncture contact portion 32 and second puncture contact portion 34 may prevent displacement of vascular closure implant 30 from puncture tract 48 by applying force to puncture tract wall 42 and compressing at least a portion of tissue 44 adjacent puncture tract wall 42, resulting in an anchoring effect of vascular closure implant 30 in puncture tract 48. The anchoring effect may oppose forces exerted on vascular closure implant 30 by blood in a vessel comprising vessel wall 46, and in fact, forces exerted on vascular closure implant 30 may further anchor vascular closure implant 30 in puncture tract 48.

FIG. 5 is an exemplary vascular closure implant 30 comprising a plug element 52 according to at least one embodiment. As illustrated in this figure, vascular closure implant 30 may comprise an anchor element 31 having a first puncture contact portion 32, a bend portion 36, and a second puncture contact portion 34. Vascular closure implant 30 may also comprise a plug element 52. As described above, first puncture contact portion 32 may be connected to bend portion 36, which may additionally be connected to second puncture contact portion 34.

Additionally, plug element 52 may be coupled to anchor element 31 of vascular closure implant 30 through any suitable coupling means. In at least one embodiment, plug element 52 may be coupled to anchor element 31 at any suitable location, including, for example, a location at and/or proximate to bend portion 36. Additionally, plug element 52 may be positioned such that it may abut vessel wall 46 at and/or proximate to the site of a vessel puncture 50 in vessel wall 46 when vascular closure implant 30 is deployed in puncture tract 48. In various embodiments, plug element 52 may contact vessel wall 46 at vessel contact portion 56. In additional embodiments, a portion of plug element 52, such as vessel contact portion 56, may at least partially fill a portion of vessel puncture 50, effectively plugging at least a portion of vessel puncture 50.

FIG. 6 is an exemplary vascular closure implant 30 comprising a plug element 52 according to an additional embodiment. As illustrated in this figure, and as described above, first puncture contact portion 32 and second puncture contact portion 34 of vascular closure implant 30 may exert force generally in directions $D_1$ and $D_2$. Additionally, vascular closure implant 30 may also exert force on plug element 52 generally in direction $D_3$, and accordingly, a portion of plug element 52, such as vessel contact portion 56, may exert force against vessel wall 46 generally in direction $D_3$ to at least partially close vessel puncture 50. In additional embodiments, plug element 52 may expand upon being positioned and/or deployed in puncture tract 48, causing vessel contact portion 56 to move and/or to exert a force against vessel wall 46 generally in direction $D_3$.

In various embodiments, anchor element 31 and plug element 52 may each comprise an absorbent and/or expandable material. For example, anchor element 31 and plug element 52 may each comprise an absorbent material that expands in the presence a liquid, such as a liquid present in blood. In at least one embodiment, anchor element 31 and plug element 52 may comprise materials having substantially the same rate of expansion. For example, anchor element 31 and plug element 52 may comprise a collagen material having substantially the same expansion rate.

In additional embodiments, anchor element 31 and plug element 52 may comprise materials having different expansion rates. In other words, anchor element 31 comprise a material having a different expansion rate than a material in plug element 52. For example, anchor element 31 and plug element 52 may comprise substantially the same material in different configurations. For example, anchor element 31 and plug element 52 may comprise collagen materials having separate expansion rates due to various differences in the characteristics of the collagen materials. In certain embodiments, anchor element 31 and plug element 52 may comprise separate materials having separate expansion rates.

FIG. 7 is an exemplary plug element 52 according to at least one embodiment. As illustrated in this figure, plug element 52 may comprise a vessel contact portion 56 and a coupling hole 54. Coupling hole 54 may comprise a hole extending into and/or through at least a portion of plug element 52. Coupling hole may be formed in any suitable portion of plug element 52 and may be configured to couple plug element 52 to a portion of vascular closure implant 30.

Figure 11:
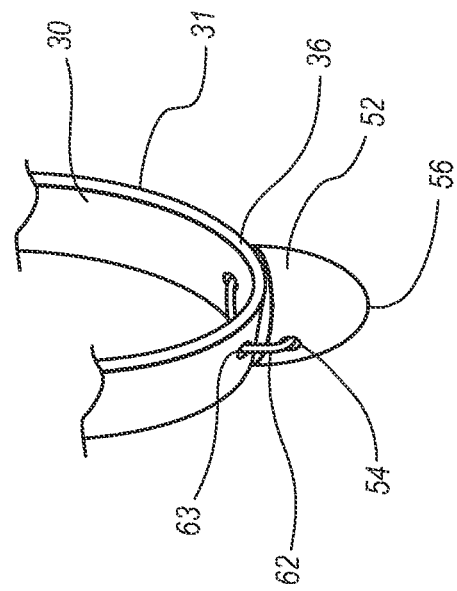
FIG. 11 is a perspective view of a bend portion of a vascular closure implant coupled to a plug element according to an additional embodiment.

For example, FIG. 11 shows a portion of vascular closure implant 30 comprising a plug element 52. As illustrated in this figure, plug element 52 is coupled to bend portion 36 of vascular closure implant 30 by a suture 62. Suture 62 may comprise any suitable material, such as, for instance, a bioabsorbable polymer, including PEG, PLA, and/or PGA. In various embodiments, suture 62 may pass through coupling hole 54 and one or more coupling holes 63 in a portion of vascular closure implant 30 to which plug element 52 is coupled. Plug element 52 may also be coupled to a portion of vascular closure implant 30 through any suitable means, including, for example, with an adhesive composition.

In addition, plug element 52 may be formed of any suitable material. According to various embodiments, plug element 52 may comprise a bioabsorbable material. Plug element 52 may also comprise a material that is relatively hard and/or which does not swell noticeably in the presence of blood. In at least one embodiment, plug element 52 may comprise a material that has a hardness greater than a material forming bend portion 36, first puncture contact portion 32, and/or second puncture contact portion 34 of vascular closure implant 30. For example, plug element 52 may comprise a polymeric material such as PEG, PLA, and/or PGA. According to certain embodiments, plug element 52 may also comprise barbs to assist in anchoring vascular closure implant to puncture tract 48 and/or vessel wall 46.

Plug element 52 comprising a relatively hard material may facilitate stable positioning of vascular closure implant 30 in puncture tract 48, since plug element 52 may be less likely to move relative to puncture tract wall 42 and/or vessel wall 46 once vascular closure implant 30 is deployed in puncture tract 48. Additionally, plug element 52 comprising a relatively hard material may facilitate tamping and/or compaction of a relatively soft and/or compressible portion of vascular closure implant 30 following positioning and/or deployment of vascular closure implant 30 in puncture tract 48. For example, plug element 52 may provide a relatively hard surface against which a relatively soft and/or compressible portion of vascular closure implant 30 may be tamped and/or compacted.

Additionally, plug element 52 may comprise a material that swells and/or expands in the presence of blood, such as collagen. In at least one embodiment, plug element 52 may expand upon being positioned and/or deployed in puncture tract 48, causing vessel contact portion 56 to move and/or to exert a force against vessel wall 46 generally in direction $D_3$ (see, e.g., FIG. 6). According to various embodiments, plug element 52 may comprise a material that swells at substantially the same rate as a material forming at least a portion of the remainder of vascular closure implant 30 (e.g., first puncture contact portion 32, bend portion 36, and/or second puncture contact portion 34). Alternatively, plug element 52 may comprise a material that swells at a faster or slower rate than a material forming at least a portion of the remainder of vascular closure implant 30. Forming plug element 52 of a material that may swell and/or expand may enable production of a vascular closure implant 30 that may apply a desired amount of force against vessel wall 46, and/or that may expand to contact and/or apply force to vessel wall 46 within a selected time following deployment of vascular closure implant 30 in puncture tract 48.

FIG. 8 is an exemplary plug element 52 according to at least one embodiment. As illustrated in this figure, plug element 52 may comprise a first plug element portion 58 and a second plug element portion 60. Second plug element portion 60 may comprise vessel contact portion 56. In various embodiments, first plug element portion 58 and a second plug element portion 60 may comprise substantially the same materials. In additional embodiments, first plug portion 58 and a second plug portion 60 may comprise different materials. According to certain embodiments, first plug element portion 58 and second plug element portion 60 may be formed to different diameters and/or different shapes. Plug element 52 comprising first plug element portion 58 and second plug element portion 60 having different diameters and/or shapes may facilitate positioning of plug element 52 in puncture tract 48 relative to and/or at least partially within vessel puncture 50 in vessel wall 46.

FIG. 9 is an exemplary plug element 52 according to an additional embodiment. As illustrated in this figure, plug element 52 may comprise a first plug element portion 58 and a second plug element portion 60 formed of different materials. For example, first plug element portion 58 may comprise a material, such as collagen, that is capable of swelling and/or expanding in the presence of various fluids such as fluids present in blood. Additionally, second plug element portion 60 may comprise a material that is relatively harder than first plug element portion 58, such as, for example, a polymeric material, which may include PGA, PEG, and/or PLA.

Figure 10:
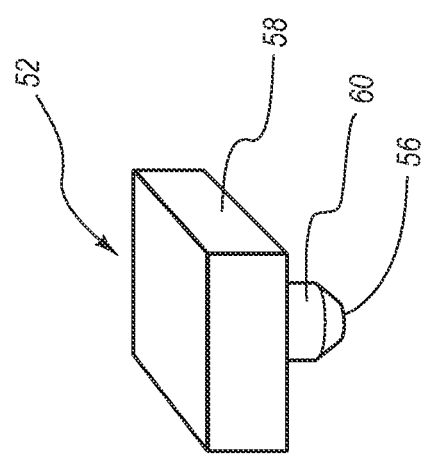
FIG. 10 is a perspective view of a plug element according to an additional embodiment.

FIG. 10 is an exemplary plug element 52 according to an additional embodiment. First plug element portion 58 and/or second plug element portion 60 may comprise various geometric configurations. For example, as illustrated in this figure, first plug element portion 58 may comprise a generally rectangular shape and second plug element portion 60 may comprise a generally cylindrical shape. Additionally, first plug element portion 58 and/or second plug element portion 60 may be formed to any suitable shape and/or size and may be formed of any suitable material and/or combination of materials.

FIGS. 12 and 13 show a side view and a front view respectively of a distal end portion of an exemplary vascular closure device 70 according to at least one embodiment. Vascular closure device 70 may comprise a proximal end portion and a distal end portion. As used in this application, a "proximal direction" may refer to a direction generally facing toward the proximal end portion of vascular closure device 70, and a "distal direction" may refer to a direction generally facing toward the distal end portion of vascular closure device 70. The proximal end portion of vascular closure device 70 device may include an end portion of the vascular closure device that is located in relatively closest proximity to an operator of the vascular closure device 70 when the vascular closure device 70 is in use (e.g., an end portion of a handle portion of vascular closure device 70). Additionally, the distal end portion of vascular closure device 70 may include an end portion of the vascular closure device that is located in relatively closest proximity to the site of a puncture tract when the vascular closure device 70 is in use. (e.g., an end portion of insertion sheath 72 of vascular closure device 70).

As illustrated in FIGS. 12 and 13, vascular closure device 70 may comprise an insertion sheath 72 and a locator wire tip 78. Locator wire tip 78 may comprise an end portion of a locator wire 96, as will be explained in greater detail below with reference to FIG. 14. Additionally, insertion sheath 72 may comprise a blood inlet hole 76 and an insertion end portion 74 as shown in FIGS. 12 and 13. Insertion sheath 72 may comprise a portion of vascular closure device 70 configured to be inserted into puncture tract 48 and/or vessel puncture 50 prior to deployment of vascular closure implant 30.

In additional embodiments, as illustrated in FIGS. 12 and 13, vascular closure device 70 may comprise an insertion sheath cavity 80 defined by and formed within insertion sheath 72. Insertion sheath cavity 80 may be configured to hold and/or protect vascular closure implant 30 prior to deployment of vascular closure implant 30. Additionally, insertion sheath 72 may aid in introducing vascular closure implant 30 into puncture tract 48. For example, vascular closure implant 30 may be positioned inside insertion sheath cavity 80 prior to insertion of insertion sheath 72 into puncture tract 48. Subsequently, insertion sheath 72 may be inserted into puncture tract 48. During insertion of insertion sheath 72 into puncture tract 48, insertion sheath 72 may assist in guiding and/or positioning vascular closure implant 30 prior to deployment of vascular closure implant 30 in puncture tract 48. Additionally, insertion sheath 72 may assist in protecting vascular closure implant 30 and/or may prevent or reduce the amount of liquid contacting vascular closure implant 30 prior to deployment of vascular closure implant 30 in puncture tract 48.

FIG. 14 is a cross-sectional side view of the distal end portion of the exemplary vascular closure device 70 illustrated in FIGS. 12 and 13 according to an additional embodiment. As illustrated in this figure, vascular closure device 70 may comprise an insertion sheath 72 and an insertion sheath cavity 80 defined by and formed within insertion sheath 72.

Figure 15:
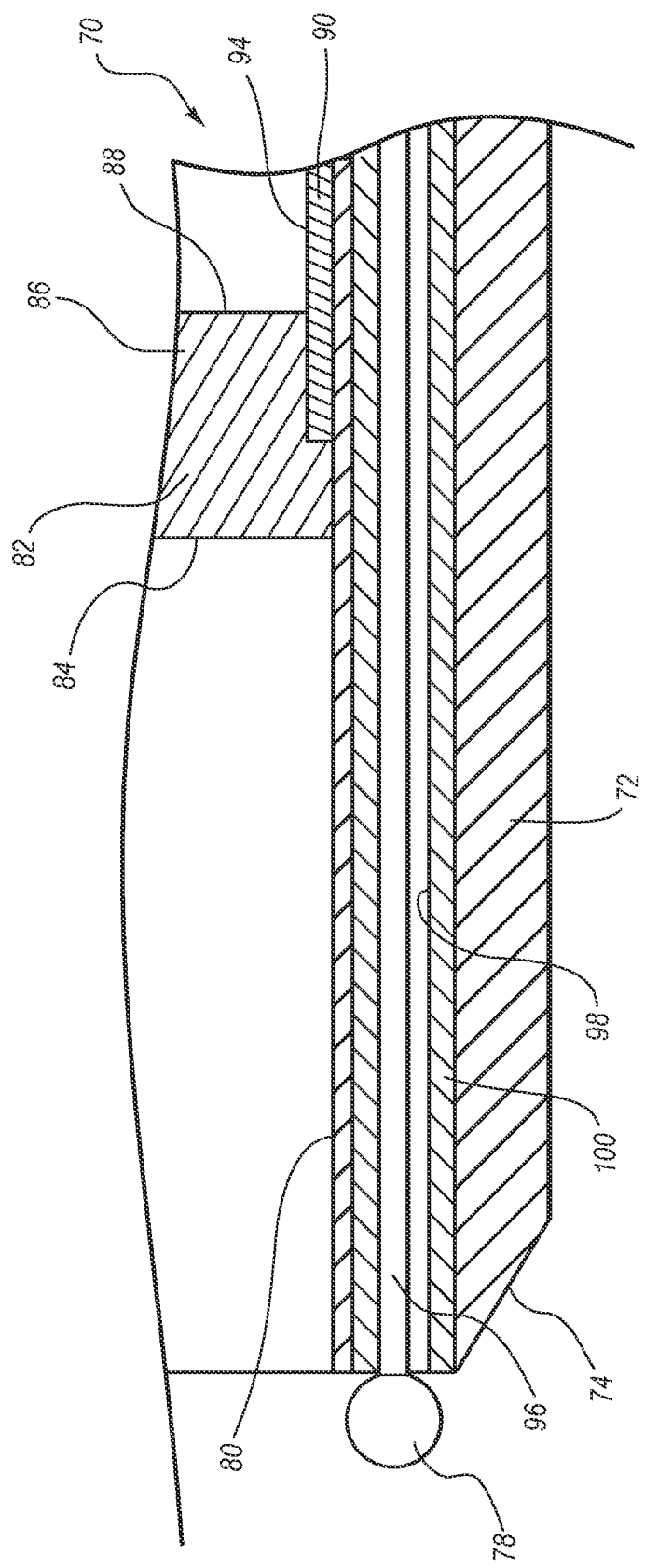
FIG. 15 is a cross-sectional view of a distal end portion of a vascular closure device according to an additional embodiment.

Vascular closure device 70 may also comprise a locator wire 96 disposed within at least a portion of insertion sheath 72. At least a portion of locator wire 96 may comprise a vessel locator for identifying at least a portion of a vessel and/or positioning vascular closure implant 30 in implant tract 48 and/or vessel puncture 50. Locator wire 96 may be positioned within any portion of insertion sheath 72. For example, locator wire 96 may be disposed within a locator passage 98, as illustrated in FIG. 14. Locator passage 98 may comprise a passage formed and/or defined within insertion sheath 72. In certain embodiments, locator passage 98 may be integrally formed with insertion sheath 72. In additional embodiments, locator passage 98 may comprise a tube disposed within at least a portion of insertion sheath 72, as will be described in greater detail below. Additionally, locator wire 96 may be disposed within insertion sheath 72 at a position radially outward from a longitudinal axis of insertion sheath cavity 80, as shown in FIG. 15. In additional embodiments, locator wire 96 may be disposed within a central portion of insertion sheath cavity 80.

Locator wire 96 may comprise an elongated member, such as, for example, a wire, a rod, a fiber, or a filament, formed of any material suitable for insertion into a blood vessel for purposes of locating at least a portion of the vessel and/or for positioning vascular closure implant 30 within puncture tract 48. Locator wire 96 may be formed to any suitable size or shape. For example, locator wire 96 may comprise a relatively thin wire having a diameter within a range of approximately 0.05 inches to approximately 0.020 inches. In at least one embodiment, locator wire 96 may be positioned within insertion sheath 72 in a generally parallel orientation relative to a lengthwise axis of vascular closure device 70.

In at least one embodiment, locator wire 96 may comprise a superelastic and/or a shape memory material having superelastic and/or shape memory characteristics, and may include, for instance, a metallic and/or a polymer material. In various embodiments, locator wire 96 may comprise an elongated member, such as a wire, formed of a superelastic and/or shape memory alloy. A suitable superelastic and/or shape memory alloy may include, without limitation, a nitinol alloy, which is a nickel titanium alloy.

According to at least one embodiment, a superelastic and/or shape memory material may include a material capable of being substantially deformed from an original shape, substantially returning to the original shape at a later time. For example, a portion of locator wire 96 comprising a superelastic and/or shape memory material may be formed to an original shape having a specific crystallographic configuration through any suitable means. Subsequently, the portion of locator wire 96 comprising a superelastic and/or shape memory material may be deformed from the original shape to a distorted shape under various conditions, loads, and/or stresses. The portion of locator wire 96 comprising a superelastic and/or shape memory material may later return to a shape substantially equivalent to the original shape under various conditions, such as when a stress and/or load maintaining the portion of locator wire 96 in the distorted shape is removed from the portion of locator wire 96.

In at least one embodiment, at least a portion of locator wire 96 may be formed into an original and/or memorized shape prior to disposing locator wire 96 within at least a portion of insertion sheath 72. As will be described in greater detail below, a portion of locator wire 96 may be formed to any original shape suitable for use in locating at least a portion of a vessel and/or for positioning vascular closure implant 30 within puncture tract 48. Locator wire 96 may retain shape memory of the original shape, even after being substantially distorted. Following formation of at least a portion of locator wire 96 to an original shape, locator wire 96 may be formed to a distorted shape that is different from the original shape. Locator wire 96 may be formed to any distorted shape suitable for placing and/or fitting locator wire 96 within insertion sheath 72 and/or locator tube 100, as will be described below. Additionally, locator wire 96 may be formed to any distorted shape suitable for deploying locator wire 96 from vascular closure device 70 into a vessel and/or a puncture tract.

Locator wire 96 may also comprise a locator wire tip 78. Locator wire tip 78 may be formed, for example, by crimping and/or melting an end portion of locator wire 96. In certain embodiments, a separate material may be adhered to an end portion of locator wire 96. Locator wire tip 78 may be formed to any shape and size suitable for enabling atraumatic introduction of locator wire into a vessel and/or puncture tract 48. In at least one embodiment, locator wire tip 78 may comprise a rounded end portion of locator wire 96. In some examples, the locator wire 96 has a non-circular cross-sectional shape such as a rectangular or oval shape. The locator wire 96 may have a taper, such as a taper in cross-sectional size from a greater size at the proximal end (e.g., for increased strength) to a smaller size at the distal end (e.g., for improved manipulation).

In additional embodiments, as shown in FIG. 14, vascular closure device 70 may comprise a displacement member 90. Displacement member 90 may comprise any element disposed in vascular closure device 70 suitable for displacing vascular closure implant 30 relative to insertion sheath 72. Displacement member 90 may be disposed at least partially within and/or adjacent insertion sheath 72. In certain embodiments, displacement member 90 may comprise a partially or substantially solid member. In additional embodiments, displacement member 90 may comprise a tubular member, as illustrated in FIG. 14.

A displacement member cavity 94 may also be at least partially defined within displacement member 90. In at least one embodiment, displacement member 90 may comprise a displacement member inlet hole 92 defined in displacement member 90 that may be at least partially aligned with blood inlet hole 76 defined in insertion sheath 72, providing a fluid conduit between an exterior of insertion sheath 72 and displacement member cavity 94, as illustrated in FIG. 14.

Additionally, a fluid barrier 82 may be disposed on and/or at least partially within an end portion of displacement member 90. For example, fluid barrier 82 may comprise an insert portion 86 disposed within an interior end portion of displacement member 90 as shown in FIG. 14. Fluid barrier 82 may also comprise an implant contact surface 84 and a blood contact surface 88. Implant contact surface 84 may be positioned within a portion of insertion sheath cavity 80 facing in a distal direction relative to vascular closure device 70. In addition, blood contact surface 88 may be positioned within a portion of displacement member cavity 94 facing in a proximal direction relative to vascular closure device 70. Fluid barrier 82 may comprise any suitable material, such as, for example, various polymeric materials, including silicone materials.

FIG. 15 is a cross-sectional view of a distal end portion of an exemplary vascular closure device 70 according to an additional embodiment. As illustrated in this figure, locator wire 96 may be disposed within a locator tube 100 within insertion sheath 72. In various embodiments, locator tube 100 may comprise any suitable material, and may comprise any shape or size of tube suitable for holding and/or deploying locator wire 96. Additionally, locator tube 100 may be positioned within at least a portion of insertion sheath 72 between insertion sheath 72 and insertion sheath cavity 80. Locator tube 100 may also be positioned between insertion sheath 72 and displacement member 90. In additional embodiments, locator tube 100 may be positioned substantially centrally within at least a portion of insertion sheath cavity 80 and/or displacement member cavity 94. In various embodiments, locator tube 100 and insertion sheath 72 may be capable of moving relative to one another, such as, for example, during deployment of vascular closure implant 30.

FIGS. 16 and 17 show, respectively, a side view and a front view of a distal end portion of an exemplary vascular closure device 70 having an expanded locator portion 102 of locator wire 96 according to at least one embodiment. As illustrated in these figures, locator wire 96 may comprise an expanded locator portion 102 on the distal end portion of vascular closure device 70, extending in a generally distal direction from insertion sheath 72 and/or locator tube 100.

In various embodiments, expanded locator portion 102 may refer to an original shape of a portion of locator wire 96 and/or may refer to a shape of a portion of locator wire 96 relatively and/or substantially equivalent to the original shape. For example, at least a portion of locator wire 96 may be formed to an original shape, following which locator wire 96 may be distorted when it is positioned within insertion sheath 72 and/or locator tube 100. In at least one embodiment, locator wire 96 may be distorted to a generally elongated shape within insertion sheath 72 and/or locator tube 100. Subsequently, locator wire 96 may be deployed to locate at least a portion of a vessel and/or at least a portion of puncture tract 48. During deployment of locator wire 96, at least a portion of locator wire 96 may be displaced from a distal end portion of insertion sheath 72 and/or locator tube 100. A portion of locator wire 96 protruding from insertion sheath 72 and/or locator tube 100 may substantially return to the original shape. Accordingly, at least a portion of locator wire 96 protruding from insertion sheath 72 and/or locator tube 100 may form expanded locator portion 102, as illustrated in FIGS. 16 and 17.

Expanded locator portion 102 may comprise any shape or size suitable for use in locating at least a portion of a vessel and/or at least a portion of puncture tract 48. In at least one embodiment, expanded locator portion 102 may comprise a shape that prevents expanded locator portion 102 from passing through a vessel puncture 50 in vessel wall 46 when expanded locator portion 102 is deployed in a vessel. Additionally, expanded locator portion 102 may be longer and/or wider than a width and/or diameter of insertion sheath 72. In certain embodiments, as shown in FIGS. 16 and 17, expanded locator portion 102 may comprise a portion of locator wire 96 that is formed in a "FIG. 8" configuration.

Figure 18:
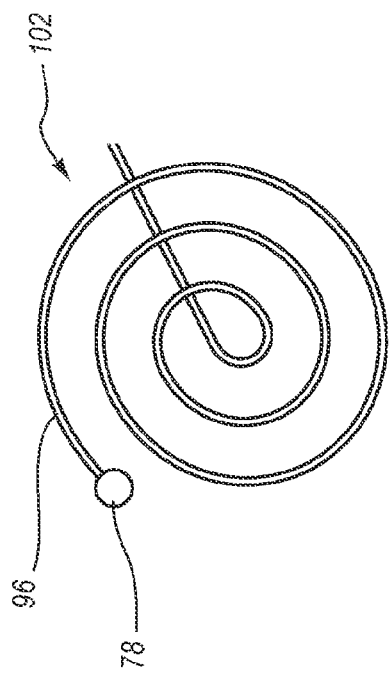
FIG. 18 is a perspective view of an expanded locator portion according to an additional embodiment.
Figure 19:
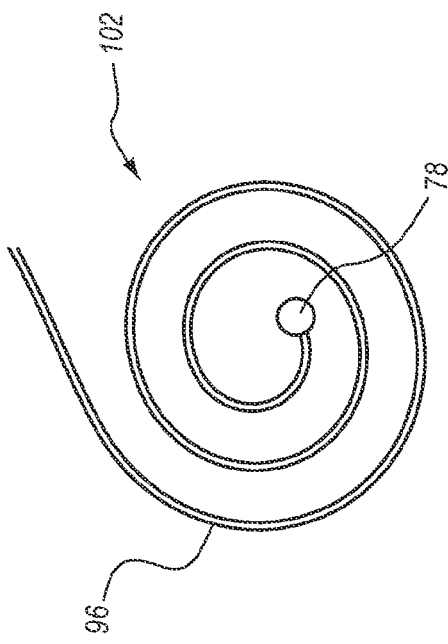
FIG. 19 is a perspective view of an expanded locator portion according to an additional embodiment.
Figure 20:
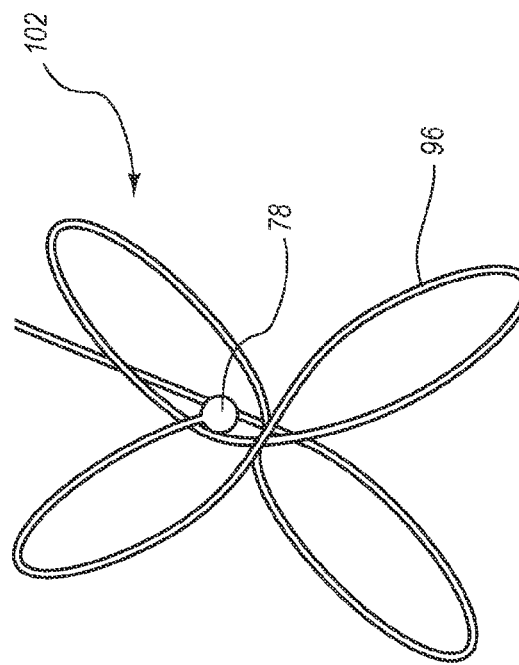
FIG. 20 is a perspective view of an expanded locator portion according to an additional embodiment.

FIGS. 18-20 show perspective views of an exemplary expanded locator portion 102 formed from a portion of locator wire 96, according to additional embodiments. As illustrated in FIGS. 18 and 19, expanded locator portion 102 may comprise a portion of locator wire 96 that is formed in a spiral configuration. In at least one embodiment, as shown in FIG. 18, expanded locator portion 102 may comprise a portion of locator wire 96 formed in a spiral configuration in which locator wire tip 78 is disposed on a radially outward portion of the spiral. In an additional embodiment, as shown in FIG. 19, expanded locator portion 102 may comprise a portion of locator wire 96 formed in a spiral configuration in which locator wire tip 78 is disposed on a radially inward portion of the spiral.

In certain embodiments, as illustrated in FIG. 20, expanded locator portion 102 may be comprise a portion of locator wire 96 that is formed in a configuration where locator wire 96 crosses over itself a plurality of times. For example, expanded locator portion 102 may comprise a portion of locator wire 96 formed in a general "clover" shape, as illustrated in FIG. 20. In additional embodiments, locator wire 96 may loop and/or cross over itself any suitable number of times and may be formed to any desired shape, without limitation.

FIG. 21 is a side view of an exemplary vascular closure device 70 disposed in a puncture tract 48 and a vessel 104 according to at least one embodiment. As illustrated in this figure, vascular closure device 70 may comprise an insertion sheath 72 that is coupled to a device handle 106. As discussed above, insertion sheath 72 may also comprise a blood inlet hole 76 and an insertion end portion 74. Vessel 104 may include any bodily vessel, including, for example, a vascular vessel.

In various embodiments, vascular closure device 70 may comprises a displacement member 90 disposed within at least a portion of insertion sheath 72. Additionally, displacement member 90 may comprise a displacement member cavity 94. As described above, displacement member 90 may comprise a displacement member inlet hole 92 defined in displacement member 90 that may be at least partially aligned with blood inlet hole 76 defined in insertion sheath 72, providing a fluid conduit between an exterior of insertion sheath 72 and displacement member cavity 94 (e.g., see FIG. 14).

In additional embodiments, vascular closure device 70 may comprise a locator wire deployment button 110, an implant deployment button 108, and a blood outlet hole 112. Locator wire deployment button 110 may be coupled to device handle 106. Additionally, implant deployment button 108 may be coupled to device handle 106.

In at least one embodiment, blood outlet hole 112 may be defined in device handle 106. Blood outlet hole 112 may be in fluid communication with blood inlet hole 76. Additionally, blood outlet hole 112 may be open to an exterior of device handle 106. In various embodiments, blood outlet hole 112 may be connected to and/or at least partially aligned with displacement member cavity 94, providing a fluid conduit between displacement member cavity 94 and an exterior of insertion sheath 72. Accordingly, blood inlet hole 76 may be in fluid communication with displacement member cavity 94, and displacement member cavity 94 may be in fluid communication with blood outlet hole 112.

In at least one embodiment, a fluid, such as blood, that enters blood inlet hole 76 may flow through displacement member cavity 94 and out blood outlet hole 112. In at least an additional embodiment, blood inlet hole 76 and blood outlet hole 112 may be connected through a channel formed in at least a portion of vascular closure device 70 other than displacement member cavity 94. For example, a conduit may be positioned between blood inlet hole 76 and blood outlet hole 112 and may be formed in at least a portion of insertion sheath 72 and/or device handle 106 separate from displacement member 90 and/or displacement member cavity 94. Optionally, blood outlet hole 112 may be defined in a portion of vascular closure device 70, such as, for example, a portion of insertion sheath 72.

In various embodiments, as illustrated in FIG. 21, a portion of vascular closure device 70 may be at least partially inserted into puncture tract 48 defined in tissue 44 by puncture tract wall 42. Additionally, a portion of vascular closure device 70 may be at least partially inserted into vessel puncture 50 formed in vessel wall 46. A portion of vascular closure device 70 may also be at least partially inserted into vessel 104, which may comprise blood flowing through vessel 104. For example, at least a portion of insertion sheath 72 of vascular closure device 70 may be at least partially inserted into puncture tract 48 (defined by puncture tract wall 42), vessel puncture 50, and/or vessel 104.

According to at least one embodiment, a portion of vascular closure device 70, such as insertion sheath 72, may be inserted into vessel 104 to a depth where blood in vessel 104 may enter blood inlet hole 76. Blood entering blood inlet hole 76 may flow through a conduit formed within vascular closure device 70 to blood outlet hole 112, and the blood may subsequently be emitted from blood outlet hole 112 to an exterior of device handle 106 and/or vascular closure device 70. Accordingly, blood emitted from blood outlet hole 112 may serve as an indicator that insertion sheath 72 has been inserted to a desired depth within vessel 104.

According to additional embodiments, after a portion of vascular closure device 70, such as insertion sheath 72, is inserted into vessel 104 to a depth where blood is emitted from blood outlet hole 112, insertion sheath 72 may be withdrawn at least partially from vessel 104 to a point where blood is no longer emitted from blood outlet hole 112. A point at which blood is no longer emitted from blood outlet hole 112 may be a point at which blood inlet hole 76 is no longer adjacent to vessel 104. In particular, a point at which blood is no longer emitted from blood outlet hole 112 may be a point at which blood inlet hole 76 is blocked by a portion of vessel puncture 50 and/or puncture tract wall 42. Blood inlet hole 76 may positioned on insertion sheath 72 in a location such that when insertion sheath 72 is withdrawn to a point at which blood is not emitted from blood outlet hole 112, at least a portion of vascular closure device 70 and/or insertion sheath 72 may remain within vessel 104, such as, for example, a distal end portion of insertion sheath 72 and/or a portion of locator wire 96 (e.g., locator wire tip 78).

FIG. 22 is a cross-sectional side view of an exemplary vascular closure device 70 disposed in a puncture tract 48 and a vessel 104 according to an additional embodiment. FIG. 22 illustrates exemplary vascular closure device 70 disposed in puncture tract 48 and vessel 104 to a depth where blood inlet hole 76 is adjacent to puncture tract wall 42. Accordingly, blood inlet hole 76 is effectively blocked by puncture tract wall 42 and is substantially separated from blood in vessel 104, as described above. As illustrated in this figure, at least a distal end portion of insertion sheath 72 and locator wire 96 may remain within vessel 104.

As illustrated in FIG. 22, vascular closure device 70 may comprise a vascular closure implant 30 disposed within insertion sheath cavity 80. Vascular closure implant 30 may be located distally from fluid barrier 82, and in certain embodiments, implant contact surface 84 of fluid barrier 82 (e.g., see FIG. 15) may be adjacent to and/or in contact with vascular closure implant 30.

Additionally, a portion of vascular closure device 70, such as, for example, device handle 106, may comprise a locator wire deployment button 110, an implant deployment button 108, and a blood outlet hole 112, as described above. Locator wire deployment button 110 may comprise any button and/or any other component suitable for deploying at least a portion of locator wire 96 within vessel 104. For example, as illustrated in FIG. 22, locator wire deployment button 110 may comprise an elongated member, a portion of which may protrude from device handle 106 such that locator wire deployment button 110 is readily accessible to an operator using vascular closure device 70. Locator wire deployment button 110 may directly and/or indirectly act on locator wire 96 to displace a portion of locator wire 96 from insertion sheath 72 and/or locator tube 100.

In various embodiments, locator wire deployment button 110 comprising an elongated member may extend in a direction generally parallel to a longitudinal axis of device handle 106. A proximal end portion 114 of locator wire deployment button 110 may be positioned adjacent to a force transferring member 116, which may be configured to transfer force from locator wire deployment button 110 directly and/or indirectly to locator wire 96. Force transferring member 116 may comprise any component suitable for transferring force from locator wire deployment button 110 to locator wire 96, including, without limitation, a gear, a lever, a spring mechanism, and/or an electrical mechanism. In at least one embodiment, as shown in FIG. 22, force transferring member 116 may comprise a lever having a first lever end portion 118, a second lever end portion 122, and a pivot portion 120. In various embodiments, a proximal end portion 114 of locator wire deployment button 110 may be positioned adjacent to first lever end 118 of force transferring member 116.

In various embodiments, a portion of vascular closure device 70, such as, for example, device handle 106, may also comprise a locator wire holding member 124, an indicator engagement member 126, an indicator 128, and an indicator engagement cavity 130. As illustrated in FIG. 22, locator wire holding member 124 may be coupled to a proximal end portion of locator wire 96. Locator wire holding member 124 may be configured to transfer force from force transferring member 116 to locator wire 96, forcing at least a portion of locator wire 96 to be displaced from insertion sheath 72 and/or locator tube 100. In various embodiments, locator wire holding member 124 may be positioned adjacent to second lever end 122 of force transferring member 116.

In various embodiments, locator wire holding member 124 may be integrally formed with, coupled to, or adjacent to indicator engagement member 126. A portion of vascular closure device 70, such as, for example, device handle 106, may also comprise an indicator 128 having an indicator engagement cavity 130 defined within indicator 128. Indicator engagement member 126 may comprise any component suitable for engaging and/or coupling with indicator engagement cavity 130 in indicator 128.

In additional embodiments, a portion of vascular closure device 70, such as, for example, device handle 106, may comprise an implant deployment button 108 coupled directly and/or indirectly to insertion sheath 72. Implant deployment button 108 may comprise any button and/or any other component suitable for deploying vascular closure implant 30. In certain embodiments, implant deployment button 108 may comprise a gear driven mechanism, allowing for implant deployment button 108 to be essentially moved or rolled into a suitable position using the gear driven mechanism. For example, implant deployment button 108 may comprise a wheel or a gear that can be manually rolled by an operator, wherein the rolling causes the wheel or gear to move relative to device handle 106.

Implant deployment button 108 may also comprise a member having a portion that may protrude from device handle 106 such that implant deployment button 108 is readily accessible to an operator using vascular closure device 70. Implant deployment button 108 may directly and/or indirectly act on insertion sheath 72 and/or vascular closure implant 30 to deploy vascular closure implant 30 from insertion sheath 72. In at least one embodiment, implant deployment button 108 may be configured to move in a generally proximal direction. As implant deployment button 108 is moved in a proximal direction, insertion sheath 72 may also move in a proximal direction while displacement member 90, and likewise, vascular closure implant 30 remain relatively stationary, thereby deploying vascular closure implant 30 from vascular closure device 70, as will be explained in greater detail below.

Figure 23:
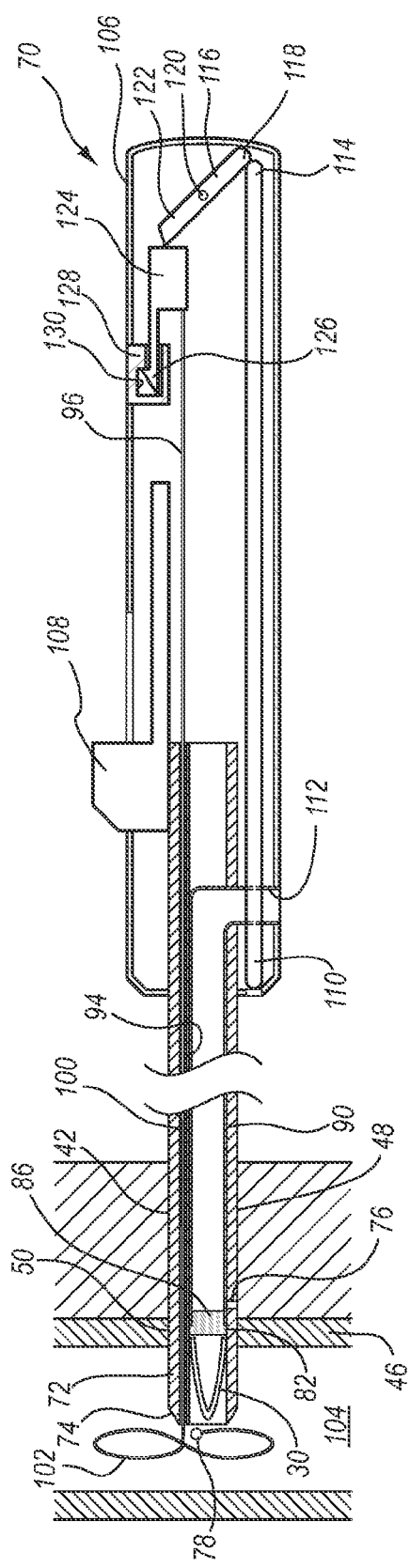
FIG. 23 is a cross-sectional side view of a vascular closure device disposed in a puncture tract according to an additional embodiment.

FIG. 23 is a cross-sectional side view of an exemplary vascular closure device 70 disposed in a puncture tract 48 and a vessel 104 according to an additional embodiment. As illustrated in this figure, a force may be applied to locator wire deployment button 110, causing a portion of locator wire 96 to be deployed within vessel 104. For example, following insertion and positioning of insertion sheath 72 within puncture tract 48 and/or vessel 104, as described above, an operator may apply a force to locator wire deployment button 110 causing locator wire 96 to be deployed within vessel 104, forming expanded locator portion 102 in vessel 104 as shown in FIG. 23.

In various embodiments, locator wire deployment button 110 may cause a portion of locator wire 96 to be deployed with vessel 104 by applying a force to force transferring member 116, which in turn may apply a force to locator wire holding member 124. In certain embodiments, proximal end portion 114 of locator wire deployment button 110 may apply a force in a generally proximal direction to first lever end portion 118 of force transferring member 116, causing force transferring member 116 to rotate about pivot portion 120. As force transferring member 116 rotates about pivot portion 120, second lever end portion 122 may move in a generally distal direction, causing second lever end portion 122 to apply a force to locator wire holding member 124 in a generally distal direction. Locator wire holding member 124, which is coupled to locator wire 96, may subsequently apply a force to locator wire 96 in a generally distal direction, causing a portion of locator wire 96 to extend from insertion sheath 72 and or locator tube 100 as illustrated in FIG. 23.

In at least one embodiment, locator wire holding member may be attached to indicator engagement member 126. As shown in FIG. 23, second lever end portion 122 may move in a generally distal direction, causing second lever end portion 122, and accordingly, indicator engagement member 126 to move in a generally distal direction. Subsequently, as illustrated in this figure, indicator engagement member 126 may be inserted within and/or become coupled to indicator engagement cavity 130 in indicator 128. Indicator 128 may comprise any suitable indicator that may provide feedback to an operator of vascular closure apparatus. For example, indicator 128 may provide visual and/or tactile feedback to indicate an amount of force applied to locator wire 96, which is coupled to indicator 128 via locator wire holding member 124.

Figure 24:
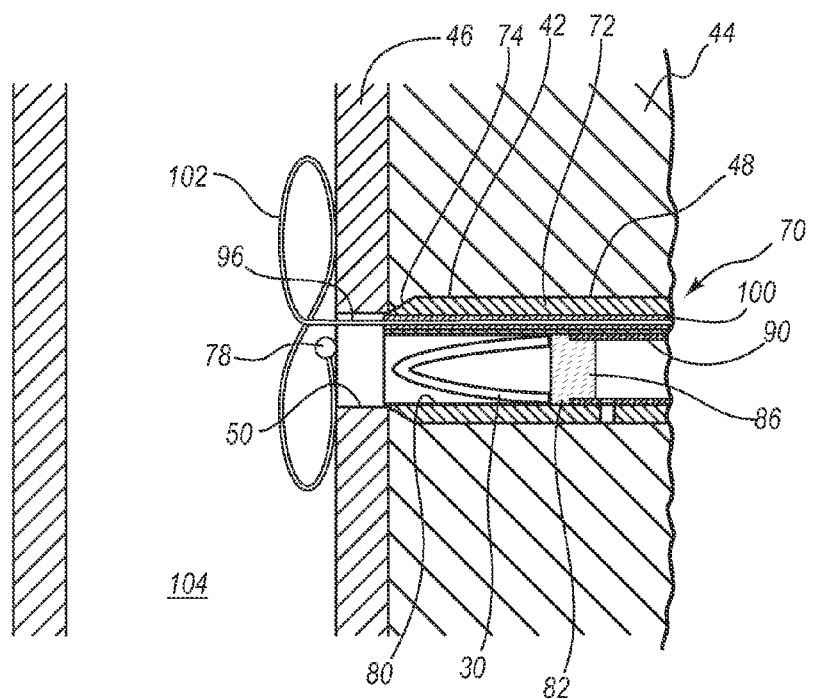
FIG. 24 is a cross-sectional side view of a distal end portion of a vascular closure device disposed in a puncture tract according to an additional embodiment.

FIG. 24 is a cross-sectional side view of a distal end of an exemplary vascular closure device 70 disposed in puncture tract 48 according to an additional embodiment. As illustrated in this figure, locator wire 96 may be deployed in vessel 104 to form expanded locator portion 102 (e.g., see FIGS. 16-20).

In at least one embodiment, following deployment of locator wire 96, insertion sheath 72 may be at least partially withdrawn from vessel 104, along with locator wire 96. For example, insertion sheath 72, which contains vascular closure implant 30 in insertion sheath cavity 80, may be at least partially withdrawn from vessel 104 until a portion of expanded locator portion 102 contacts a portion of vessel wall 46. Upon contacting vessel wall 46, indicator 128 may indicate that insertion sheath 72 is positioned within puncture tract 48 at a depth suitable for deployment of vascular closure implant 30. In certain embodiments, as insertion sheath 72 is at least partially withdrawn from vessel 104, and a portion of expanded locator portion 102 contacts a portion of vessel wall 46, a force may be applied to locator wire 96 by vessel wall 46, for example, which in turn applies a force to indicator 128, causing indicator 128 to visually and/or tactilely indicate that insertion sheath 72 is suitably positioned within puncture tract 48 relative to vessel 104.

Figure 25:
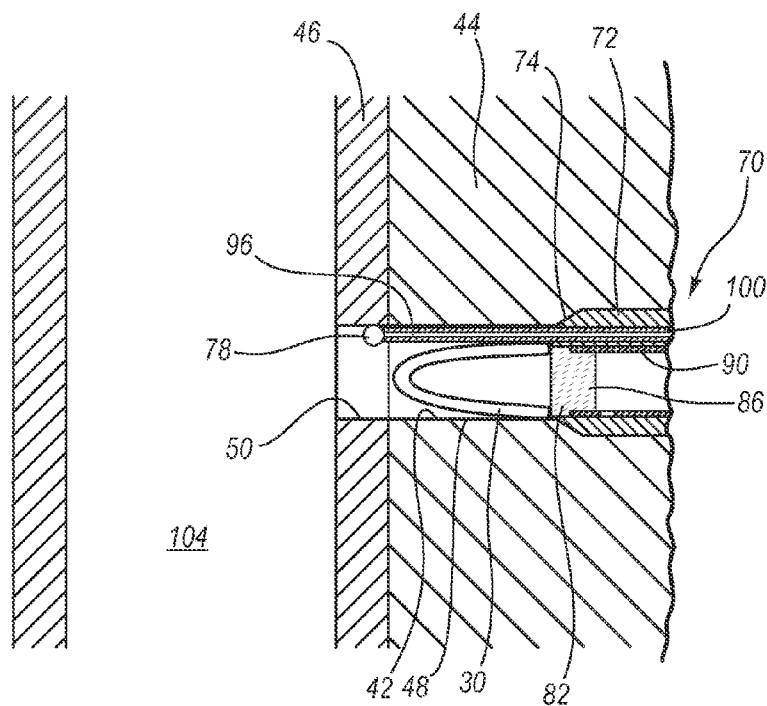
FIG. 25 is a cross-sectional side view of a distal end portion of a vascular closure device disposed in a puncture tract according to an additional embodiment.

FIG. 25 is a cross-sectional side view of a distal end of an exemplary vascular closure device 70 disposed in puncture tract 48 according to an additional embodiment. Once insertion sheath 72 is suitably positioned within puncture tract 48, as described above with reference to FIG. 24, vascular closure implant 30 may be deployed within puncture tract 48.

In at least one embodiment, as illustrated in FIG. 25, vascular closure implant 30 may be deployed by moving insertion sheath 72 in a generally proximal direction relative to closure implant 30. Insertion sheath 72 may be moved in a generally proximal direction by moving implant deployment button 108 in a generally proximal direction, as described above (e.g., see FIG. 23). As insertion sheath 72 is moved in a generally proximal direction, displacement member 90 may remain relatively stationary within puncture tract 48. Accordingly, vascular closure implant 30 may remain relatively stationary as insertion sheath 72 is moved in a generally proximal direction, and accordingly, vascular closure implant 30 may be positioned outside insertion sheath 72 following positioning of insertion sheath 72 in a proximal direction relative to vascular closure implant 30, as illustrated in FIG. 25.

In additional embodiments, as insertion sheath 72 is moved in a generally proximal direction, locator tube 100 may remain relatively stationary within puncture tract 48. Additionally, as illustrated in FIG. 23, locator wire 96 may be coupled to locator wire holding member 124. In certain embodiments, a portion of implant deployment button 108 may be adjacent and/or in close proximity to locator wire holding member 124 and/or indicator 129. Accordingly, as implant deployment button 108 is moved in a relatively proximal direction, a portion of implant deployment button 108 may cause locator wire holding member 124 and/or locator wire 96 to move in a relatively proximal direction. As locator wire 96 is moved in a relatively proximal direction, locator wire 96 may be retracted into locator tube 100, which remains relatively stationary in puncture tract 48 and is extended relative to insertion sheath 72, as shown in FIG. 25. With locator wire 96 disposed within locator tube 100, as illustrated in FIG. 25, vascular closure device 70 may be removed from puncture 48, leaving vascular closure implant 30 disposed within puncture tract 48. Additionally, with locator tube 100 located to a side of vascular closure implant 30 as shown in FIG. 25, vascular closure implant 30 may be readily deployed from insertion sheath 72 without inadvertently dislodging vascular closure implant 30 during withdrawal of insertion sheath 72 and/or locator tube 100 from puncture tract 48.

Figure 26:
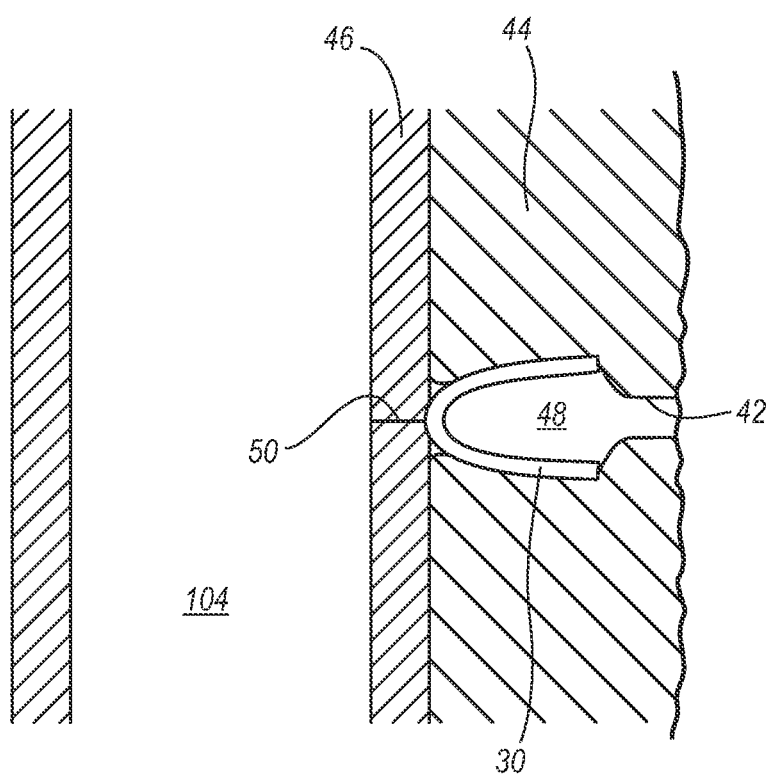
FIG. 26 is a side view of a vascular closure implant disposed in a puncture tract according to an additional embodiment.

FIG. 26 is a side view of an exemplary vascular closure implant 30 disposed in a puncture tract 48 according to an additional embodiment. As described above, vascular closure device 70 may be removed from puncture tract 48, leaving vascular closure implant 30 disposed within puncture tract 48. As illustrated in FIG. 26, vascular closure implant 30 may be disposed within puncture tract 48 adjacent to and/or at least partially within vessel puncture 50, effectively sealing at least a portion of vessel puncture 50 and/or puncture tract 48 and preventing blood from migrating from vessel 104 through vessel puncture 50 and/or puncture tract 48 (e.g., see FIGS. 3 and 4). As described above, vascular closure implant 30 may exert force on puncture tract wall 42 and or vessel puncture 50. Additionally, vascular closure implant 30 may absorb fluids present in blood contacting vascular closure implant 30, causing vascular closure implant 30 to swell and/or expand within puncture tract 48 and/or vessel puncture, further sealing at least a portion of vessel puncture 50 and/or puncture tract 48. The tip of the implant can potentially be inside the arteriotomy wall using the implant swelling property and the limited stretching capability of the tissue to create a sandwich effect.

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. It is desired that the embodiments described herein be considered in all respects illustrative and not restrictive and that reference be made to the appended claims and their equivalents for determining the scope of the instant disclosure.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising."

What is claimed is:

1. A vascular closure implant, comprising:
    an anchor element, the anchor element comprising:
        an expandable material;
        a first puncture contact portion having a first lateral width;
        a bend portion connected to the first puncture contact portion, the bend portion including a bend, the bend having a distal facing surface, the bend portion having a bend lateral width;
        a second puncture contact portion connected to the bend portion, the first puncture contact portion, bend portion, and second puncture contact portion forming a continuous line in a U-shape or V-shape, the bend portion being configured to be positioned proximate to the site of a vessel puncture in a vessel wall relative to the first and second puncture contact portions upon deployment in a vessel puncture tract, the first and second puncture contact portions being configured to each engage different lateral sides of the vessel puncture tract, the second puncture contact portion having a second lateral width, wherein the bend lateral width is less than or equal to the first and second lateral widths;
    a plug element coupled to the bend portion of the anchor element, the plug being removably attached to the distal facing surface of the bend, the plug element comprising a first plug portion and a second plug portion, the first plug portion comprising a first material, the second plug portion comprising a second material, the first material being different from the second material.

2. The vascular closure implant of claim 1, wherein the expandable material of the anchor element and the expandable material of the plug element have differing expansion rates.

3. The vascular closure implant of claim 1, wherein the bend portion is capable of exerting a force on the first puncture contact portion in a first general direction and a force on the second puncture contact portion in a second general direction.

4. The vascular closure implant of claim 3, wherein the force exerted on the first puncture contact portion substantially opposes the force exerted on the second puncture contact portion.

5. The vascular closure implant of claim 1, wherein the anchor element comprises an elastically deformable material.

6. The vascular closure implant of claim 1, wherein the anchor element comprises an absorbent material.

7. The vascular closure implant of claim 1, wherein the anchor element comprises collagen.

8. The vascular closure implant of claim 1, wherein the plug element comprises an absorbent material.

9. The vascular closure implant of claim 1, wherein the plug element comprises collagen.

10. The vascular closure implant of claim 1, wherein the plug element comprises a material having a hardness greater than a hardness of the anchor element.

11. The vascular closure implant of claim 1, wherein the first plug portion and the second plug portion have different shapes.

12. The vascular closure implant of claim 1, wherein the first and second puncture contact portions are configured to expand due to mechanical energy stored in the bend portion.

13. A vascular closure implant, comprising:
    an anchor element, the anchor element comprising:
        an expandable material;
        a first puncture contact portion having a first lateral width;
        a bend portion connected to the first puncture contact portion, the bend portion including a bend, the bend having a distal facing surface, the bend portion having a bend lateral width, the bend portion being configured to store mechanical energy;
        a second puncture contact portion connected to the bend portion, the first puncture contact portion, bend portion, and second puncture contact portion forming a continuous line in a U-shape or V-shape, the bend portion being configured to be positioned proximate to the site of a vessel puncture in a vessel wall relative to the first and second puncture contact portions upon deployment in a vessel puncture tract, the first and second puncture contact portions each having proximal-most tips, the proximal-most tips being configured to apply laterally-directed anchoring forces to opposite lateral sides of the vessel puncture tract on release of the mechanical energy, the second puncture contact portion having a second lateral width, wherein the bend lateral width is less than or equal to the first and second lateral widths;
    a plug element coupled to the bend portion of the anchor element, the plug being removably attached to the distal facing surface of the bend, the plug element comprising an expandable material.

14. The vascular closure implant of claim 13, wherein the laterally-directed forces are configured to anchor the anchor element against the vessel puncture tract.

15. The vascular closure implant of claim 13, wherein the bend portion is configured to store mechanical energy upon bending deformation of the bend portion.

16. The vascular closure implant of claim 13, wherein the bend portion is configured to store the mechanical energy upon folding of the anchor element at the bend portion.

17. A vascular closure implant, comprising:
an anchor element, the anchor element comprising:
  an expandable material;
  a first puncture contact portion having a first lateral width;
  a bend portion connected to the first puncture contact portion, the bend portion including a bend, the bend having a distal facing surface, the bend portion having a bend lateral width;
  a second puncture contact portion connected to the bend portion, the first puncture contact portion, bend portion, and second puncture contact portion forming a continuous line in a U-shape or V-shape, the bend portion being configured to be positioned proximate to the site of a vessel puncture in a vessel wall relative to the first and second puncture contact portions upon deployment in a vessel puncture tract, the first and second puncture contact portions being configured to each engage different lateral sides of the vessel puncture tract, the second puncture contact portion having a second lateral width, wherein the bend lateral width is less than or equal to the first and second lateral widths;
a plug element coupled to the bend portion of the anchor element, the plug being removably attached to the distal facing surface of the bend, the plug element comprising an expandable material, the plug element comprising a first cylindrical portion and a second cylindrical portion, the first cylindrical portion having a first diameter, the second cylindrical portion having a second diameter, the first diameter being different from the second diameter.

18. The vascular closure implant of claim 17, wherein the first cylindrical portion comprises a first material, the second cylindrical portion comprises a second material, and the first material is different from the second material.

* * * * *